US009580695B2

(12) United States Patent
Li et al.

(10) Patent No.: US 9,580,695 B2
(45) Date of Patent: Feb. 28, 2017

(54) REDUCTION OF TOBACCO-SPECIFIC NITROSAMINES USING GENETIC MODIFICATION TO ELEVATE PRODUCTION OF NATIVE ANTIOXIDANTS IN TOBACCO

(75) Inventors: Qinglin Li, Richmond, VA (US); Marc Robert Krauss, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 1706 days.

(21) Appl. No.: 11/300,590

(22) Filed: Dec. 15, 2005

(65) Prior Publication Data
US 2006/0260014 A1 Nov. 16, 2006

Related U.S. Application Data

(60) Provisional application No. 60/638,170, filed on Dec. 23, 2004.

(51) Int. Cl.
*C12N 15/82* (2006.01)
*A01H 5/12* (2006.01)
*C12N 9/02* (2006.01)
*C12N 9/04* (2006.01)

(52) U.S. Cl.
CPC ......... *C12N 9/0008* (2013.01); *C12N 9/0006* (2013.01); *C12N 15/8243* (2013.01)

(58) Field of Classification Search
USPC ...................................................... 800/317.3
See application file for complete search history.

(56) References Cited

U.S. PATENT DOCUMENTS

| | | | | |
|---|---|---|---|---|
| 3,845,774 | A | * | 11/1974 | Tso et al. .............. 131/309 |
| 5,378,619 | A | | 1/1995 | Rogers |
| 5,516,671 | A | * | 5/1996 | Lawrence et al. ........ 800/279 |
| 5,654,414 | A | * | 8/1997 | Ryals et al. ............. 800/279 |
| 5,792,932 | A | * | 8/1998 | Marco et al. ............ 800/288 |
| 5,989,846 | A | | 11/1999 | Klessig et al. |
| 6,018,100 | A | | 1/2000 | Rogers |
| 6,024,318 | A | * | 2/2000 | Barry ..................... 242/406 |
| 6,054,318 | A | * | 4/2000 | Murray et al. ........... 435/418 |
| 6,121,511 | A | * | 9/2000 | Chou ..................... 800/294 |
| 6,187,571 | B1 | * | 2/2001 | Pignard et al. .............. 435/6 |
| 6,310,272 | B1 | | 10/2001 | Ohashi et al. |
| 6,818,806 | B1 | | 11/2004 | Gray et al. |
| 2003/0000538 | A1 | * | 1/2003 | Bereman ................. 416/17 |
| 2003/0056801 | A1 | | 3/2003 | Krauss et al. |
| 2004/0072218 | A1 | | 4/2004 | Quan Pan |

FOREIGN PATENT DOCUMENTS

| | | |
|---|---|---|
| WO | WO 99/04013 | 1/1999 |
| WO | WO 02/38588 | 5/2002 |

OTHER PUBLICATIONS

Murray et al. Expression of Talromyces flavus glucose oxidase gene in cotton and tobacco reduces fungal infection, but is also phytotoxic. 1999. Molec. Breeding 5:219-232.*
http://en.wikipedia.org/wiki/Adolph_Wilhelm_Hermann_Kolbe.*
Karlowski et al (2003, Plant Mol. Biol. 52:121-133).*
Grbić (2002, Physiol. Plant. 116:416-422).*
Salinas-Mondragón et al (1999, Plant Mol. Biol. 40:579-590).*
Gepstein et al (2003, Plant J. 36:629-642).*
Yang et al. (The wound-inducible Lls1 gene from maize is an orthologue of the Arabidopsis Acd1 gene, and the LLS1 protein is present in non-photosynthetic tissues, 54 Plant Mol. Biol. No. 2, 175-191 (2004)).*
GenBank Acession No. NC_003554, "Figwort Mosaic Virus, Complete Genome" Nov. 22, 2004.
Schardl et al., "Design and construction of a versatile system for the expression of foreign genes in plants," Gene, 1987, vol. 61, pp. 1-11.
Bhattacharyy et al. "Analysis of cis-sequence of subgenomic transcript promoter from the Figwort mosaic virus and comparison of promoter activity with the cauliflower mosaic virus promoters in monocot and dicot cells," Virus Research 2002, vol. 90, pp. 47-62.
Padidam M. et al., "Chemical-Inducible, Ecdysone Receptor-Based Gene Expression System for Plants" Transgenic Res. Feb. 2003;12(1):101-9.
Padidam M., "Chemically Regulated Gene Expression in Plants" Curr Opin Plant Biol. Apr. 2003;6(2):169-77.
Roslan H.A. et al., "Characterization of the Ethanol-Inducible alc Gene-Expression System in Arabidopsis Thaliana" Plant J. Oct. 2001;28(2):225-35.
Ouwerkerk P.B. et al., "Glucocorticoid-Inducible Gene Express in Rice" Planta. Jul. 2001;213(3):370-8.
Zuo J. et al., "Chemical-Inducible Systems for Regulated Expression of Plant Genes" Curr Opin Biotechnol. Apr. 2000;11(2):146-51.
Ohme-Takagi M. et al., "Regulation of Ethylene-Induced Transcription of Defense Genes" Plant Cell Physiol. Nov. 2000;41(11):1187-92.
Guo H.S. et al., "A Chemica-Regulated Inducible RNAi System in Plants" Plant J. May 2003;34(3):383-92.
Sanchez J.P. et al., "Regulation of Gene Expression in Arabidopsis Thaliana by Artificial Zinc Finger Chimeras" Plant Cell Physiol. Dec. 2002;43(12):1465-72.
Moller S.G. et al., "Chemical Regulated Production of cDNAs from Genomic DNA Fragments in Plants" Plant J. Nov. 2002;32(4):615-22.
Zuo J. et al., "Chemica-Regulated, Site-Specific DNA Excision in Transgenic Plants" Nat Biotechnol. Feb. 2001;19(2):157-61.
Zuo J. et al., "Tehnical Advance: An Estrogen Receptor-Based Transactivator XVE Mediates Highly Inducible Gene Expression in Transgenic Plants" Plant J. Oct. 2000;24(2):265-73.

(Continued)

*Primary Examiner* — Anne Kubelik
(74) *Attorney, Agent, or Firm* — Buchanan Ingersoll & Rooney PC

(57) ABSTRACT

Cured tobacco having a lower concentration of tobacco specific nitrosamines, can be produced from a transgenic tobacco plant having a heterologous nucleotide sequence encoding a polypeptide that catalyzes production of active oxygen species. The heterologous nucleotide sequence is operably coupled to a regulatory nucleotide sequence that directs expression of the polypeptide. The regulatory nucleotide sequence can include constitutive and/or inducible promoter elements.

9 Claims, No Drawings

(56) References Cited

OTHER PUBLICATIONS

Nishiuchi T. et al., "Wound-Induced Expression of the FAD7 Gene Is Mediated by Different Regulatory Domains of Its Promoter in Leaves/Stems and Roots" Plant Physiol., Dec. 1999, vol. 121, pp. 1239-1246.

Martinez-Hernandez A. et al., "Functional Properties and Regulatory Complexity of a Minimal RBCS Light-Responsive Unit Actived by Phytochrome, Cryptochrome, and Plastid Signals" Plant Physiol., Apr. 2002, vol. 128, pp. 1223-1233.

Yen S-K et al., "Environmental and Developmental Regulation of the Wound-Induced Cell Wall Protein WI12 in the Halophyte Ice Plant" Plant Physiol., Oct. 2001, vol. 127, pp. 517-528.

Bernier et al., "Germins and Germin-Like Proteins: Plant Do-All Proteins. But What Do They Do Exactly?" Plant Physiol. Biochem. 39 (2001) pp. 545-554.

Barnes, "Variable Patterns of Expression of Luciferase in Transgenic Tobacco Leaves" Proc. Natl. Acad. Sci. USA, Dec. 1990, vol. 87, pp. 9183-9187.

Wycoff K. et al., "Stress Activation of a Bean Hydroxyproline-Rich Glycoprotein Promoter Is Superimposed on a Pattern of Tissue-Specific Developmental Expression" Plant Physiol. (1995) 109; pp. 41-52.

Berrocal-Lobo M. et al., "Snakin-2, an Antimicrobial Peptide from Potato Whose Gene Is Locally Induced by Wounding and Responds to Pathogen Infection" Plant Physiol., Mar. 2002, vol. 128, pp. 951-961.

Qin X. et al., "Overexpression of a 9-cis-Epoxycarotenoid Dioxygenase Gene in Nicotiana plumbaginifolia Increases Abscisic Acid and Phaseic Acid Levels and Enhances Drought Tolerance" Plant Physiol., Feb. 2002, vol. 128, pp. 544-551.

Wu G. et al., "Activation of Host Defense Mechanisms by Elevated Production of $H_2O_2$ in Transgenic Plants" Plant Physiol. (1997) 115; 427-435.

Wu G. et al., "Disease Resistance Conferred by Expression of a Gene Encoding $H_2O_2$-Generating Glucose Oxidase in Transgenic Potato Plants" the Plant Cell, Sep. 1995, vol. 7, pp. 1357-1368.

Berna A. et al., "Regulated Expression of a Wheat Germin Gene in Tobacco: Oxalate Oxidase Activity and Apoplastic Localization of the Heterologous Protein" Plant Molecular Biology, 33:417-429, 1997.

Berna A. et al., "Regulation by Biotic and Abiotic Stress of a Wheat Germin Gene Encoding Oxalate Oxidase, a $H_2O_2$-Producing Enzyme" Plant Molecular Biology, 39:539-549, 1999.

Rushton P. et al., "Synthetic Plant Promoters Containing Defined Regulatory Elements Provide Novel Insights into Pathogen- and Wound-Induced Signaling" The Plant Cell, Apr. 2002, vol. 14, pp. 749-762.

Gepstein S. et al., "Large-Scale Identification of Leaf Senescence-Associated Genes" The Plant Journal (2003) 36, 629-642.

John Gray et al., *Light-Dependent Death of Maize lls1 Cells Is Mediated by Mature Chloroplasts*, 130 Plant Physiology 1894-1907 (Dec. 2002).

William M. Gray et al., *Role of the Arabidopsis Ring-H2 Protein RBX1 in Rub Modification and SCF Function*, 14 The Plant Cell 2137-2144 (Sep. 2002).

Michael et al., *The First 50 Plant Genomes*, 6(2) The Plant Genome pp. 1-7 (Jul. 2013).

Gray et al., *Arabidopsis thaliana lethal leaf-spot 1 homolog (Lls1) mRNA, partial cds*, GenBank U77347.1, http://www.ncbi.nlm.nih.gov/nuccore/U77347.1 (Apr. 15, 1997).

Gray et al., *Arabidopsis thaliana accelerated cell death 1 (ACD1) mRNA, complete cds*, GenBank AY344061.1 http://www.ncbi.nlm.nih.gov/nuccore/37962885?sat=34&satkey=1044063 (Nov. 1, 2003).

Gray et al., *Arabidopsis thaliana LLS1-like protein mRNA, complete cds*, GenBank AY344062.1, http://www.ncbi.nlm.nih.gov/nuccore/AY344062.1 (Nov. 1, 2003).

Southwick et al., *Arabidopsis thaliana lethal leaf-spot 1 homolog Lls1 (At3g44880) mRNA, complete cds*, GenBank AY093092.1http://www.ncbi.nlm.nih.gov/nuccore/AY093092.1 (Apr. 21, 2002).

Jwa et al., *Oryza sativa LLS1 protein (Lls1) mRNA, complete cds*, GenBank AF284781.1 http://www.ncbi.nlm.nih.gov/nuccore/AF284781.1 (Oct. 16, 2000).

Gray et al., *Zea mays lethal leaf-spot 1 (llsl) mRNA, partial cds*, GenBank U77345.1, http://www.ncbi.nlm.nih.gov/nuccore/U77345 (Apr. 15, 1997).

\* cited by examiner

REDUCTION OF TOBACCO-SPECIFIC NITROSAMINES USING GENETIC MODIFICATION TO ELEVATE PRODUCTION OF NATIVE ANTIOXIDANTS IN TOBACCO

CROSS-REFERENCE TO RELATED APPLICATION

This application hereby claims priority from Provisional Application Ser. No. 60/638,170, filed on Dec. 23, 2004, which is herein incorporated by reference in it's entirety.

BACKGROUND OF THE INVENTION

Field of the Invention

The invention relates to methods of producing tobacco having reduced levels of tobacco specific nitrosamines in the cured leaves and transgenic tobacco plants for producing tobacco having reduced levels of tobacco specific nitrosamines in the cured leaves.

Description of the Related Art

In many organisms, antioxidant activity increases upon exposure to conditions that increase the formation of active oxygen species such as hydrogen peroxide. There is evidence that active oxygen species are ubiquitous messengers in plants that stimulate defense responses against stressful conditions.

It has been reported that tobacco specific nitrosamines (TSNAs) are produced primarily in the curing process. It is believed that antioxidants interfere with the nitrosation of secondary alkaloids thereby reducing the formation of TSNAs. Commonly owned U.S. application Ser. No. 10/235,636 discloses a method for reducing tobacco specific nitrosamine content in cured tobacco by increasing the levels of antioxidants in the tobacco prior to harvesting. The methods disclosed in that application include root pruning prior to harvesting, severing the xylem tissue prior to harvesting, and administering antioxidants or chemicals that produce an increase in antioxidants to the tobacco plant after harvesting. U.S. application Ser. No. 10/235,636 and all publications referred to below are hereby incorporated into the present application entirely and for all purposes.

U.S. Pat. No. 5,516,671 discloses that plants, for example potatoes, can be transformed with a gene encoding glucose oxidase to produce plants that are resistant to disease. See also, Wu et al. (Plant Physiology, 115:427-435, 1997).

Berna and Bernier (*Plant Molecular Biology*, 33:417-29, 1997) have shown that wheat germin has oxalate oxidase (OxO) activity and (*Plant Molecular Biology*, 39:539-49, 1999) that the promoter of the gemin gf-2.8 gene is active in transgenic tobacco. Indeed, most germins and many germin-like proteins have OxO activity. (Bernier and Berna, *Plant Physiology and Biochemistry*, 39:545-9, 2001). PCT Application Publication Number WO 99/04013 discloses the expression of oxidase enzymes as a method of producing resistance to stress in a variety of plants.

Published U.S. Application No. 2004/007218 discloses a method for determination of the level of $H_2O_2$ in a cell by measuring expression of a reporter polypeptide from a promoter that is inducible by $H_2O_2$.

SUMMARY

By supplying a source of active oxygen species, for example hydrogen peroxide, that is independent of stress and/or that amplifies a response to stress, increased concentrations of antioxidant molecules can be induced in tobacco thereby providing for lower levels of tobacco specific nitrosamines in the cured tobacco.

We describe cured tobacco having reduced levels of tobacco specific nitrosamines, which is produced from a transgenic tobacco plant comprising a heterologous nucleotide sequence encoding a polypeptide that catalyzes production of active oxygen species. Of course, the heterologous nucleotide sequence is operably coupled to a regulatory nucleotide sequence that directs expression of the polypeptide. In preferred embodiments, the polypeptide that catalyzes production of active oxygen species is an oxidase, for example an oxidase selected from among oxalate oxidase and glucose oxidase. In various exemplary embodiments, the regulatory nucleotide sequences can comprise a constitutively active promoter, an inducible promoter, or elements that direct a level of constitutive expression of the polypeptide and inducible increased levels of expression. In preferred embodiments, the promoter is an inducible promoter or comprises a promoter element can be induced by treating the plant with an inducer, which can be physical and/or chemical. For example, various known plant promoters can be induced by a plant wounding treatment (e.g. root pruning or cutting the xylem tissue), chemical inducers, heat, light, drying, combinations of the foregoing, and the like.

A method of producing cured tobacco having reduced concentrations of tobacco-specific nitrosamines is disclosed. In preferred embodiments, the method comprises growing a transgenic tobacco plant having a heterologous nucleotide sequence encoding a polypeptide that catalyzes production of active oxygen species, for example as described above. The heterologous nucleotide sequence is coupled to a regulatory nucleotide sequence that directs expression of the polypeptide. The transgenic tobacco is harvested and cured.

In preferred variations of the method, the transgenic tobacco plant comprises an inducible promoter or inducible promoter elements operably coupled to the heterologous nucleotide sequence encoding a polypeptide that catalyzes production of active oxygen species. In some variants of the method, the promoter may be arranged to produce a level of constitutive expression of the polypeptide and a higher level of expression in response to an inducer. Where the promoter is an inducible promoter or comprises inducible promoter elements, the method preferably further comprises treating the tobacco to induce expression of the polypeptide prior to or at about the time of harvest. For example the tobacco may be treated with an inducer sufficient to induce expression of the polypeptide about 1 week or less prior to harvest, between about 1 to 3 weeks prior to harvest, or more than about 3 weeks prior to harvest. Alternatively, or in addition, the tobacco may be treated with an inducer at the time of harvest or within about 48 hours after harvest. In some embodiments, the natural process of senescence or the physical process of harvesting may comprise the inducer so that further treatment of the plant is unnecessary to induce expression.

DETAILED DESCRIPTION OF THE PREFERRED EMBODIMENTS

Cured tobacco that has lower levels of tobacco specific nitrosamines (TSNAs) can be produced from a transgenic tobacco plant that comprises a heterologous nucleotide sequence encoding a polypeptide that catalyzes production of active oxygen species where the heterologous nucleotide sequence is operably coupled to a regulatory nucleotide sequence that directs expression of the polypeptide.

Without wishing to be bound by theory, it is believed that the production of active oxygen species triggers defense responses in the tobacco plant that include the production of antioxidants. It is believed that such antioxidants interfere with the nitrosation of secondary alkaloids thereby reducing the formation of TSNAs. Preferred tobacco varieties of tobacco plants include Burley, Oriental, and bright. Burley is a most preferred variety.

Active oxygen species include, for example, peroxides such as hydrogen peroxide ($H_2O_2$), $O_2^-$, and $OH^+$. In preferred embodiments, the polypeptide that catalyzes production of active oxygen species is an oxidase, for example an oxidase selected from among oxalate oxidase and glucose oxidase. Other polypeptides, including proteins, which catalyze the production of active oxygen species are known to those skilled in the art, for example, acyl coA oxidase, aspartate oxidase, choline oxidase, copper amine oxidase, eosinophil peroxidase, flavin oxidase, galactose oxidase, glycolate oxidase, monoamine oxidase, polyamine oxidase, NADPH oxidase, xanthine oxidase, and the like.

Preferred oxidase enzymes include germin-like oxalate oxidase and glucose oxidase. Oxolate oxidase (OxO) catalyzes the degradation of oxalic acid into $H_2O_2$ and $CO_2$. The coding sequence of a germin-like OxO gene was isolated and genetically engineered for constitutive expression in plants by Bernier and Berna (*Plant Physiology and Biochemistry*, 39:545-9, 2001). Wu et al. (Plant Physiology, 115:427-435, 1997) created a transgenic potato plant expressing a fungal glucose oxidase gene that demonstrates some resistance to pathogens. The level of accumulation of salicylic acid in the leaves of the potato plant increased and the production mRNA's of defense related genes encoding anionic peroxidase and chitins were also induced. Constitutively elevated levels of $H_2O_2$ appear to activate an array of host defense mechanisms including the production of antioxidants.

As used herein, heterologous nucleotide sequence means a nucleotide sequence, such as a gene sequence or the coding sequence of a gene, which is derived from a different organism than the host organism in which it has been placed and/or a nucleotide sequence, which may include a sequence native to the host organism, that has been cloned from its native location and manipulated so as to be coupled with sequence with which it is not naturally coupled. For example a sequence encoding a native protein may be coupled to a non-native promoter sequence, a native promoter sequence can be coupled to a non-native protein, or native protein and promoter sequences that are naturally found in different genes may be couple and reintroduced into a host organism. A transgenic plant is a plant having a heterologous nucleotide sequence in its cells. Reliable methods for cloning a heterologous nucleotide sequence and introducing the heterologous gene into plant cells so as to produce a transgenic plant are well known to the skilled practitioner.

Regulatory sequences include those sequences necessary for transcription and/or translation of a coding sequence. For example, regulatory sequences of a gene generally include a promoter sequence. Promoters can be constitutively active, providing for continuous expression of a gene, or may be inducible, providing for expression of a gene in response to an inducer stimulus. A promoter may also comprise elements that provide for a level of constitutive expression coupled to elements that provide a higher level of expression in response to one or more inducers.

A preferred type of promoter is a tissue specific promoter, which can provide for a tissue specific expression profile, for example where expression is greatest in the roots and stems of a plant. Exemplary types of inducible promoter include stress response promoters, light inducible promoters, and chemically inducible promoters, such as promoters that are inducible by active oxygen species or another stress response product and/or by compounds produced in response to high light exposure and/or by synthetic compounds. Using a stress response promoter to express a heterologus source of active oxygen species can provide amplification of a stress response to a physical or chemical treatment.

In preferred embodiments, the regulatory nucleotide sequences can comprise a constitutively active promoter, an inducible promoter, or elements that direct a level of constitutive expression of the polypeptide and inducible increased levels of expression. In exemplary embodiments, the inducible promoter or promoter elements can be induced by plant wounding treatment, for example by root pruning or cutting the xylem tissue of a tobacco plant. In alternative embodiments, the inducible promoter can be induced by treatments such as chemical, heat, light, drought, combinations thereof, and other treatments chosen according to the known properties of the regulatory sequence.

If desired, a tissue specific promoter may be used to direct expression of the polypeptide to a chosen part of the tobacco plant. For example, a root specific promoter can be used to direct greater expression of the polypeptide in the roots. A preferred example of a tissue specific promoter includes the Figwort mosaic virus (FMV) sub-genomic transcript (Sgt) promoter and various modified varieties of the FMV Sgt promoter, such as the fragment of the FMV Sgt promoter comprising from about position −270 to about +31. This fragment was shown to be about two times stronger than the CMV 35S promoter in tobacco and to demonstrate a tissue specific expression in tobacco root that is greater than in leaf and stem. (Bhattacharyya et al., Virus Research, 90:47-62, 2002). The complete FMV genome can be found in the NCBI database under accession no. NC_003554. Other FMV promoter sequences are disclosed in U.S. Pat. Nos. 6,018,100 and 5,378,619.

If desired, expression of the polypeptide encoded by the heterologous nucleotide sequence can be regulated by a promoter that responds to natural signals associated with senescence. For example, a promoter may be chosen from among the promoters of senescence-associated genes (SAGs). Many such genes have been identified. (Gepstein et al., The Plant Journal, 36:629-42, 2003). Temporal patterns of gene expression during senescence have been observed. Thus, gene promoters can be chosen that have a level of constitutive activity, but are strongly upregulated during senescence. Among this group are promoters driving expression of cationic amino acid transporters, amino acid permease, and metallothionin. Promoters can be chosen from SAGs that are upregulated early in senescence. Among this group are promoters of the RING-H2 finger protein and the promoter of the xylose isomerase gene. Alternatively, a promoter can be chosen that is upregulated in the late stages of senescence. Among this type of promoter is the lethal leaf spot 1 (lls1) gene promoter. The use of a SAG promoter as a regulatory nucleotide sequence can permit timing the expression of the heterologous nucleotide sequence to coincide with natural events or treatments that precede harvest by a desired period. Alternatively, or in addition, because certain SAG promoters can be strongly upregulated by stress events such as leaf detachment, the use of selected SAG promoters can provide for upregulation of expression due to natural or artificial stressors and/or at the time the tobacco is harvested. When a SAG promoter is used, it may be unnecessary to further treat transgenic tobacco to obtain expression of a polypeptide that catalyzes production of active oxygen species for a desired period prior to and/or at the time of harvest.

If desired, a chemically inducible promoter can be chosen to permit induction of expression of the polypeptide in response to a non-natural signal. The regulatory sequence can comprise recognition elements that bind an engineered transcriptional activator. And the transgenic tobacco may be designed to produce a ligand binding transcriptional activator. For example, a glucocorticoid-inducible transcriptional activator (GVG) can be constructed comprising a Gal4 binding domain, a VP16 activation domain, and a gluccocorticoid receptor. Expression from a GVG activated promoter can be induced using micromolar concentrations of dexamethasone (DEX). (Ouwerkerk et al., Planta, 213:370-8, 2001). Examples of binary vectors using DEX inducible promoters can be found in GenBank under accession nos. AF294979-AF294982. As further examples, synthetic transcriptional activators comprising the ligand binding domain of the ecdysone receptor from spruce budworm, a VP16 activation domain and GAL4 and LexA DNA binding domains can be used to respond to methoxyfenozide to induce a heterologous nucleotide sequence operable coupled to a Gal4 or LexA-response element in a synthetic promoter. Alternatively, native inducible promoter elements can be coupled to the heterologous nucleotide sequence to drive inducible expression. An induction treatment could be performed by spraying or irrigation. The use of chemically inducible promoters, including field use with induction by registered agrochemicals, has been reviewed by Zuo (Current Opinion in Biotechnology, 11: 146-51, 2000).

Promoters that can be used as nucleotide regulatory sequences include synthetic plant promoters comprising a plurality of cis-acting elements. For example, various responsive elements can be inserted upstream of a minimal promoter segment such as a minimal CMV 35S promoter segment. (Rushton et al., The Plant Cell, 14:749-62, 2002). Tandem repeats may be used to increase the response of a promoter. Additional copies of elements can increase constitutive expression in addition to an inducible response. Such a synthetic promoter can also be designed to have tissue specificity, such as a preference for expression in root over expression in leaf.

A wide variety of additional suitable regulatory sequence elements and their properties are known to those of skill in the art. For example, the cauliflower mosaic virus 35S promoter is commonly used for constitutive expression. The arabidopsis FAD7 promoter provides both constitutive expression and wound induced expression. Wound responsive elements of the FAD7 promoter have been characterized. (Nishiuichi et al., *Plant Physiology*, 121-1239-46, 1999). Thus, a modified FAD7 promoter can be constructed comprising all or part of the FAD7 promoter. When using such a promoter, induction may be by wounding or by providing a chemical source of the wound response messengers that can directly induce the promoter. The hydroxyproline-rich glycoprotein (HRGP4.1) promoter from bean demonstrates a tissue specific expression profile of reporter gene that is 7-fold higher in root than stem and 10-fold higher in stem than in leaves of transgenic tobacco. The HRGP4.1 promoter also exhibits a stress response that provides for localized induction in response to wounding. (Wycoff et al., *Plant Physiology*, 109:41-42, 1995). The KatA promoter of *Agrobaterium tumefacines* is an example of a promoter that is inducible by active oxygen species such as $H_2O_2$. Quan Pan, Published U.S. Patent Application No. 2004/0072218. The Early-Light Inducible Protein 2 (ELIP2) promoter is induced by messengers triggered by strong light exposure in a pathway that is independent of hydrogen peroxide. (Kimura et al., *Photochem Photobiol.* 77:668-74, 2003). CMA5 is a native 52-bp fragment of the *Nicotiana plumbaginifolia* rbcS 8B promoter, which contains an I- and a G-box cis-element. CMA5 behaves as a light-responsive minimal unit capable of activating a heterologous minimal promoter in a phytochrome-, cryptochrome-, and plastid-dependent manner. (Martinez-Hernandez et al., *Plant Physiology*, 128:1223-33, 2002). These examples are illustrative of the various types promoters that may be chosen, but should not be considered limiting.

Expression driven by inducible promoters can be induced according to the characteristics of the chosen promoter either directly by introduction of chemical messengers or by various treatments including wounding, heat, light, drought, combinations thereof, and the like. One skilled in the art is capable of selecting and operably coupling appropriate regulatory sequence elements to a coding sequence to provide induction of polypeptide expression in response to a chosen stimulus.

A method of producing cured tobacco having reduced concentrations of tobacco-specific nitrosamines can comprise growing a transgenic tobacco plant, preferably having one or a combination of the preferred characteristics described above.

When the regulatory nucleotide sequence of the heterologous nucleotide sequence comprises an inducible promoter, or inducible promoter elements coupled to additional promoter elements, the method can preferably comprise causing induction of the promoter prior to harvest, or at harvest. In preferred embodiments, this permits the tobacco plant to grow without strong constitutive expression of stress response genes while providing for controlled induction of a strong response at a desired time. It may also be desirable to have a level of constitutive expression prior to induction. Induction may be accomplished by any treatment consistent with the nature of the chosen inducible promoter. Induction treatment can be performed prior to harvest, for example more than about 3 weeks prior to harvest, in the interval about 1 to 3 weeks prior to harvest, or less than about 3 weeks prior to harvest, such as about 48 hours prior to harvest. As described above, no separate induction treatment may be needed where the transgenic tobacco comprises a promoter that responds to natural senescence signals. Optionally, the act of harvesting may provide the inducing stimulus, or recently harvested tobacco may be treated to induce the promoter, for example tobacco may be treated with an appropriate inducer within about 48 hours of harvest.

Harvesting and curing of the tobacco may be conducted according to conventional methods. Curing is most preferably done by air curing. Conventional air-curing tobacco barns typically utilize natural convection, with air flow generally proceeding from the bottom of the barn toward the top of the barn. In curing tobacco by the procedure generally referred to as the "bulk curing" method, tobacco leaves are typically loaded in a relatively compact mass on racks or in containers and placed inside of an enclosed curing barn where a furnace or a plurality of heaters circulate a forced flow of heated air through the mass of tobacco leaves to effect curing and drying. Conventional tobacco curing barns attempt to obtain the desired atmospheric conditions such as temperature and humidity within the tobacco barn by various adjustments of louvers or openings in the sides of the barn and the operation of heaters spaced along the floor of the barn with respect to the prevailing temperature and moisture content of the outside atmosphere, the wind velocity and its direction with respect to the tobacco barn.

It may be desirable to utilize a method for curing tobacco as described in commonly owned Published U.S. Patent Application No. 2003/0145867, which is incorporated by reference herein in its entirety. Briefly, such a preferred method for air curing tobacco includes the tobacco being hung in an enclosure having one or more vertically arranged air ducts positioned near the middle of the enclosure, one or more in-line fans positioned in the air ducts, one or more ventilating fans located in an upper part of the enclosure and at least one closeable opening in a side wall of the enclosure. The method includes opening at least one opening, and operating at least one ventilating fan to force air down through the tobacco from the upper portion of the enclosure. The method of curing tobacco can include the steps of closing an opening, introducing an aqueous solution or steam into a lower portion of a vertically arranged air duct, and operating fans to diffuse the moisture upwards through the air duct.

While the invention has been described in detail with reference to preferred embodiments thereof, it will be apparent to one skilled in the art that various changes can be made, and equivalents employed, without departing from the scope of the invention.

What is claimed is:

1. Cured tobacco having lower concentrations of tobacco specific nitrosamines, comprising:
    cured leaves of a transgenic tobacco plant comprising a heterologous nucleotide sequence encoding oxalate oxidase or glucose oxidase polypeptide,
wherein the heterologous nucleotide sequence is operably coupled to a regulatory nucleotide sequence that directs expression of the polypeptide,
wherein the regulatory nucleotide sequence comprises a promoter sequence that is a lethal leaf spot 1 (lls1) gene promoter.

2. The tobacco of claim 1, wherein the tobacco is Burley tobacco.

3. A method of producing cured tobacco having reduced concentrations of tobacco-specific nitrosamines, the method comprising,
    growing a transgenic tobacco plant comprising a heterologous nucleotide sequence encoding oxalate oxidase or glucose oxidase polypeptide, wherein the heterologous nucleotide sequence is operably coupled to a regulatory nucleotide sequence that directs expression of the polypeptide, wherein the regulatory nucleotide sequence comprises a promoter sequence that is a lethal leaf spot 1 (lls1) gene promoter;
    harvesting the tobacco; and,
    curing the tobacco.

4. The method of claim 3, comprising causing induction of the promoter within the period about 3 weeks prior to harvesting the tobacco to about 48 hours after harvesting the tobacco.

5. The method of claim 3, wherein the promoter is induced by plant wounding.

6. The method of claim 3, comprising causing induction of the promoter about 1 to 3 weeks prior to harvesting the tobacco.

7. The method of claim 3, wherein the promoter is induced by one or more natural signals associated with senescence.

8. The method of claim 3, further comprising root pruning and/or severing the xylem tissue of the tobacco plant prior to harvesting.

9. The method of claim 3, wherein the tobacco is Burley tobacco.

* * * * *